(12) United States Patent
Eskander

(10) Patent No.: US 12,394,515 B1
(45) Date of Patent: Aug. 19, 2025

(54) RANDOMIZATION METHODS FOR HEALTHCARE SCHEDULING OPTIMIZATION USING PERIOPERATIVE STAGES

(71) Applicant: OPEXC Inc., Oakville (CA)

(72) Inventor: Jean-Pierre Eskander, Oakville (CA)

(73) Assignee: OPEXC INC., Oakville (CA)

( * ) Notice: Subject to any disclaimer, the term of this patent is extended or adjusted under 35 U.S.C. 154(b) by 0 days.

(21) Appl. No.: 18/899,783

(22) Filed: Sep. 27, 2024

(51) Int. Cl.
  *G16H 10/60* (2018.01)
  *G06Q 10/06* (2023.01)
  *G16H 40/20* (2018.01)

(52) U.S. Cl.
  CPC .................. *G16H 40/20* (2018.01)

(58) Field of Classification Search
  CPC ..................................... G16H 40/20
  See application file for complete search history.

(56) References Cited

U.S. PATENT DOCUMENTS

| | | | |
|---|---|---|---|
| 8,208,619 B2 | 6/2012 | Perrin et al. | |
| 8,924,238 B1 | 12/2014 | Nidy et al. | |
| 11,264,128 B2 * | 3/2022 | Brown | G16H 50/20 |
| 11,380,436 B2 | 7/2022 | Vegas Santiago et al. | |
| 11,631,037 B2 | 4/2023 | McBride et al. | |
| 2007/0073556 A1 | 3/2007 | Lau et al. | |
| 2009/0164236 A1 | 6/2009 | Gounares et al. | |
| 2010/0106517 A1 | 4/2010 | Kociubinski et al. | |
| 2014/0108035 A1 | 4/2014 | Akbay et al. | |
| 2018/0174079 A1 | 6/2018 | Choi et al. | |
| 2018/0358131 A1 | 12/2018 | Teodoro et al. | |
| 2019/0013095 A1 | 1/2019 | Lawrie | |
| 2020/0066397 A1 | 2/2020 | Rai et al. | |
| 2021/0193302 A1 * | 6/2021 | Day | G06Q 10/0631 |

* cited by examiner

*Primary Examiner* — Maroun P Kanaan
(74) *Attorney, Agent, or Firm* — Smart & Biggar LP

(57) ABSTRACT

Randomization methods for healthcare scheduling optimization using perioperative stages. Poor scheduling of surgical appointments and procedures in operating rooms can lead to unnecessary downtime, and therefore loss of efficiency. The randomization methods include various probability models, Monte Carlo simulations, and stochastic optimization is used to optimize procedure scheduling in operating rooms. The optimized schedule may be based on estimated procedure duration, estimated turn-around-time, estimated cancellation frequency, forecasted emergency operating room usage, estimated surgeon utilization, and hospital site configuration. A probabilistic machine learning model may be trained based on historic data and ongoing performance data to automate the optimization process and increase accuracy based on up-to-date information and statistics.

10 Claims, 12 Drawing Sheets

○ › Overview › By Week › Daily Insights

Recommendations : Daily Insights

Summary of Recommendations and Warnings.

📅 08/08/2024

Recommendations — 802

| OR | Program | Surgeon | Type | Case Type | Utilization Impact | (Min) |
|---|---|---|---|---|---|---|
| OR4 | URO | Doctor 1 | Add Case | TRANSURETHRAL RESECTION BLADDE | +9% | 38 |
| OR4 | URO | Doctor 1 | Add Case | CIRCUMCISION (ADULT) | +12% | 53 |
| OR4 | URO | Doctor 2 | Add Case | CYSTOSCOPY CHANGE OF URETERAL | +10% | 42 |
| TOTAL | | | | | | 133 |

🏥 Hospital 1 ▾   Refresh ⟳

Warnings — 804

| OR's | Description |
|---|---|
| OR1 | Conformation to standard turnaround time is critical to finish room on time. |
| OR1 | OR planned cases are likely to run over by 13 minutes. |
| OR4 | Block is under scheduled by at least one collectable case. |
| OR4 | Conformation to standard turnaround time is critical to finish room on time. |

FIG. 8

◎ › Dashboard › [Prime Time Utilization]

Surgical Management : Utilization By Surgeons
Overview of summary and activity

[📅 Last Week] Jul 21 - Jul 27, 2024          ● Utilization  ○ Underutilization          [🏥 Hospital 1 ▼] [Refresh ⟳]

[ORTHO]  GEN   GYN   URO                                                                ○ Programs  ● Surgeons

Utilization by Surgeon
Program utilization details by surgeon

| Surgeon Name   | Utilization % |      | No. of Blocks | Available Time | No. of Cases | Collectable Time |
|----------------|---------------|------|---------------|----------------|--------------|------------------|
| Doctor 1 (Ortho) | ▨▨▨▨▨▨▨▨▨ | 96%  | 2             | 14 Hrs 40 Min  | 7            | 0 Min            |
| Doctor 2 (Ortho) | ▨▨▨▨▨▨▨▨▨ | 92%  | 1             | 7 Hrs 20 Min   | 4            | 0 Min            |
| Doctor 3       | ▨▨▨▨▨▨▨▨▨ | 94%  | 1             | 7 Hrs 20 Min   | 4            | 0 Min            |
| Doctor 4       | ▨▨▨▨▨▨▨▨▨ | 90%  | 2             | 14 Hrs 40 Min  | 8            | 0 Min            |
| Doctor 5       | ▨▨▨▨▨▨▨▨▨ | 95%  | 1             | 7 Hrs 20 Min   | 4            | 0 Min            |
| Total          | ▨▨▨▨▨▨▨▨▨ | 93%  | 7             | 51 Hrs 20 Min  | 27           | 0 Min            |

FIG. 11

RANDOMIZATION METHODS FOR HEALTHCARE SCHEDULING OPTIMIZATION USING PERIOPERATIVE STAGES

TECHNICAL FIELD

Example embodiments relate to service scheduling such as health care resource schedule.

BACKGROUND

A healthcare system needs to manage multiple appointments to effectively care for the patients. Optimal use of time is an important factor in improving successful outcomes when patients interact with the healthcare system. For example, surgical patients suffer from excessive wait times which stem from the foundation of having limited resources to meet a surplus of demand. In some countries, such as Canada, the delay to be seen is further enhanced by Canada having a public health care system. To mitigate the patient pain of excessive wait times, existing solutions from government and third parties include increasing provider operational hours and the development of centralized booking systems. Also, some governments are moving towards funding patients to be seen at private clinics. Some drawbacks to existing solutions include, and are not limited to: increased payroll and machine operation costs from longer service hours, the inertia of culture transformation that occurs from the replacement of existing booking systems and data integrations, and the large funding to cover patient exams at private clinics which is not aligned with a public healthcare mandate. In some cases, the public healthcare system has limited resources, a surplus of demand, and suffers from the high costs of unfulfilled appointments due to no-shows, emergencies, and inadequate preparation.

It would therefore be advantageous to provide systems and methods for unfulfilled appointment prediction and optimization to be filled by patients who wish to schedule a sooner appointment.

SUMMARY

Example embodiments relate to systems and methods for prediction and optimization of resources such as scheduling appointments, practitioners, and operating rooms for providers such as medical clinics or hospitals.

Example embodiments relate to software, methods, and systems for optimizing the end-to-end perioperative process using stochastic optimization to improve efficiency and reduce unutilized rooms or appointments.

An example embodiment is a method of scheduling, comprising: receiving data relating to at least one healthcare procedure; processing the data using a machine learning model, the processing comprising applying one or more probability models to the data, performing one or more iterations of a Monte Carlo simulation on the data to calculate the collective time for provision of the at least one healthcare procedure, applying a stochastic optimization to the one or more iterations of the Monte Carlo simulation, determining an expected completion time for each of the at least one healthcare procedure taking place with a healthcare resource, based on the results of the stochastic optimization, determining, based on the expected completion time for each of the at least one healthcare procedure taking place with the healthcare resource, availability for one or more healthcare procedures with the healthcare resource; and generating a schedule of the one or more healthcare procedures to take place with the healthcare resource.

In a further example embodiment, the healthcare procedure is at least one surgical procedure, and wherein the healthcare resource is an operating room.

In a further example embodiment, the at least one surgical procedure corresponds to an entire perioperative process of the surgical procedure.

In a further example embodiment, determining the expected completion time includes using sub-models of the machine learning model to predict duration of sequential perioperative sub-stages of each of the at least one surgical procedure, and wherein the determining the expected completion time includes aggregating the predicted duration of the sequential perioperative sub-stages for each of the at least one surgical procedure.

In a further example embodiment, the duration of the sequential perioperative sub-stages include pre-anesthesia duration, patient positioning duration, surgery duration, and post anesthesia duration.

In a further example embodiment, determining the expected completion time of each of the at least one surgical procedure includes using sub-models of the machine learning model to predict pre-anesthesia equipment usage, cancellation frequency, and/or surgical emergency frequency.

In a further example embodiment, the Monte Carlo simulations are applied over at least 10,000 iterations.

In a further example embodiment, the probability model includes actual surgical duration for each surgical procedure, procedure volume changes, cancellation rates for each surgical procedure, and/or combined emergency surgical rates.

In a further example embodiment, the cancellation rates for each surgical procedure are categorized based on the day of the week.

In a further example embodiment, cancellation frequency is calculated based on a binomial distribution.

In a further example embodiment, the combined emergency surgical rates are modeled using a Poisson distribution.

In a further example embodiment, the stochastic optimization process accounts for uncertainty in variables related to pre-Covid and post-Covid differences, healthcare resource specialization, and/or healthcare procedure-specific differences.

In a further example embodiment, the stochastic optimization process is based on a site configuration of a location containing the healthcare resource.

In a further example embodiment, determining the availability for one or more healthcare procedures is based on duration of the one or more healthcare procedures, importance of the one or more healthcare procedures, or availability of the one or more healthcare resources.

In a further example embodiment, the method further comprises generating for display the one or more healthcare procedures for at least one of a website, an interactable web page, or a graphical user interface.

Another example embodiment is a computer-implemented method for service optimization, comprising: receiving, from a first database, a historical dataset; receiving, from a second database, performance data relating to a service, wherein the service includes at least one healthcare procedure; processing the historical dataset and the performance data, wherein the processing comprises filtering the historical dataset and the performance data into discrete groups identified by type of healthcare procedure, calculating an expected completion time for each healthcare procedure, and calculating a standard deviation for each expected completion time for each healthcare procedure; creating a first training set comprising the processed historical dataset and the processed performance data; and training a machine learning model using the first training set.

In a further example embodiment, the at least one healthcare procedure is at least one surgical procedure.

In a further example embodiment, wherein the training includes training sub-models of the machine learning model to predict duration of sequential perioperative sub-stages of the at least one surgical procedure.

In a further example embodiment, the duration of sequential perioperative sub-stages include pre-anesthesia duration, patient positioning duration, surgery duration, and post anesthesia duration.

In a further example embodiment, the training includes training sub models of the machine learning model to predict pre-anesthesia equipment usage, cancellation frequency, and/or surgical emergency frequency.

In a further example embodiment, the method further comprises creating, by the trained machine learning model, a second training set comprising second processed historical dataset, second processed performance data, second calculated expected completion time for the one or more healthcare procedures, and a second set of performance data, and training the machine learning model on the second training set.

Another example embodiment is a computer device, including a processor configured to perform any of the above examples of the method.

Another example embodiment is a non-transitory memory containing instructions which, when executed by a processor, cause the processor to perform any of the above examples of the method.

BRIEF DESCRIPTION OF THE DRAWINGS

Reference will now be made, by way of example, to the accompanying drawings which show example embodiments, and in which:

FIG. 8 illustrates an exemplary user interface for displaying daily recommendations;

FIG. 11 illustrates an exemplary user interface for providing healthcare practitioner utilization statistics.

Similar reference numerals may have been used in different figures to denote similar components.

DETAILED DESCRIPTION

Example embodiments relate to systems and methods for scheduling optimization software for providers such as hospitals and medical clinics. Example embodiments relate to systems and methods for healthcare vacancy prediction and optimization to be filled by patients whose scheduled healthcare procedures are estimated to fit within a vacancy in a healthcare resource.

Figure 1:
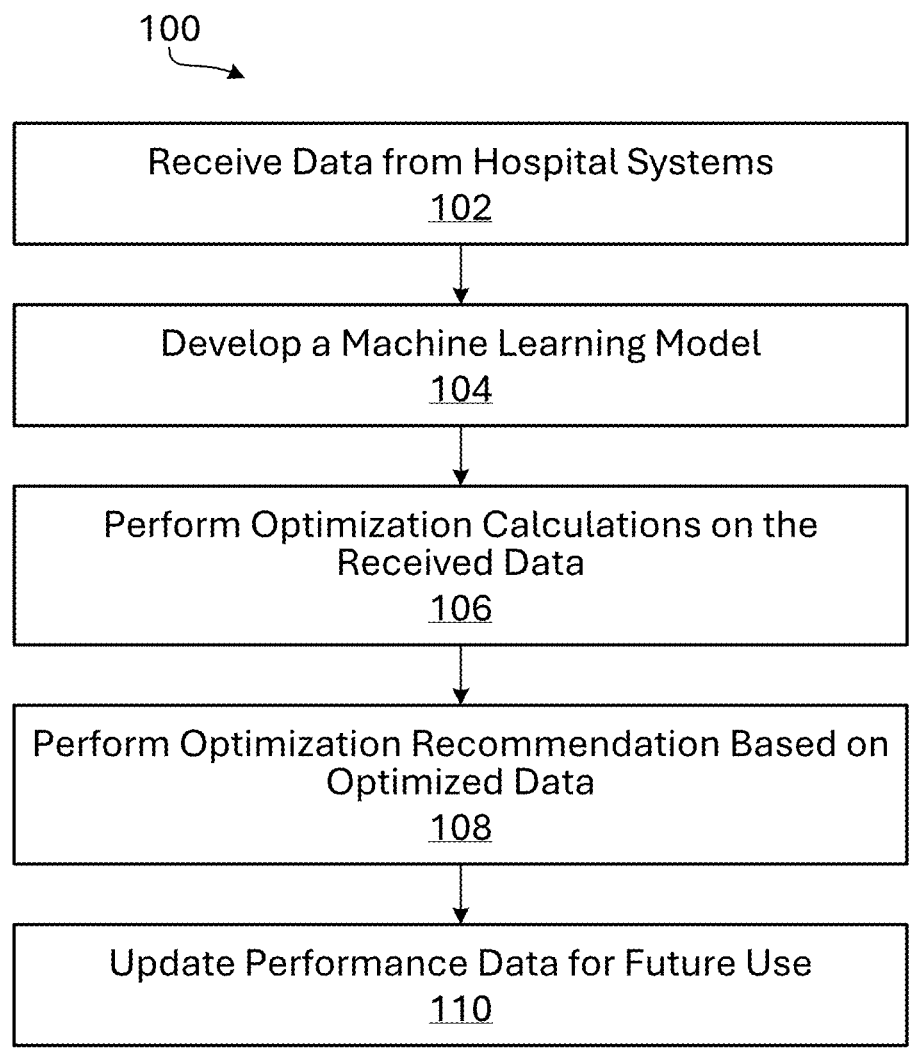
FIG. 1 illustrates a flowchart for an exemplary patient service optimization procedure.
Figure 2:
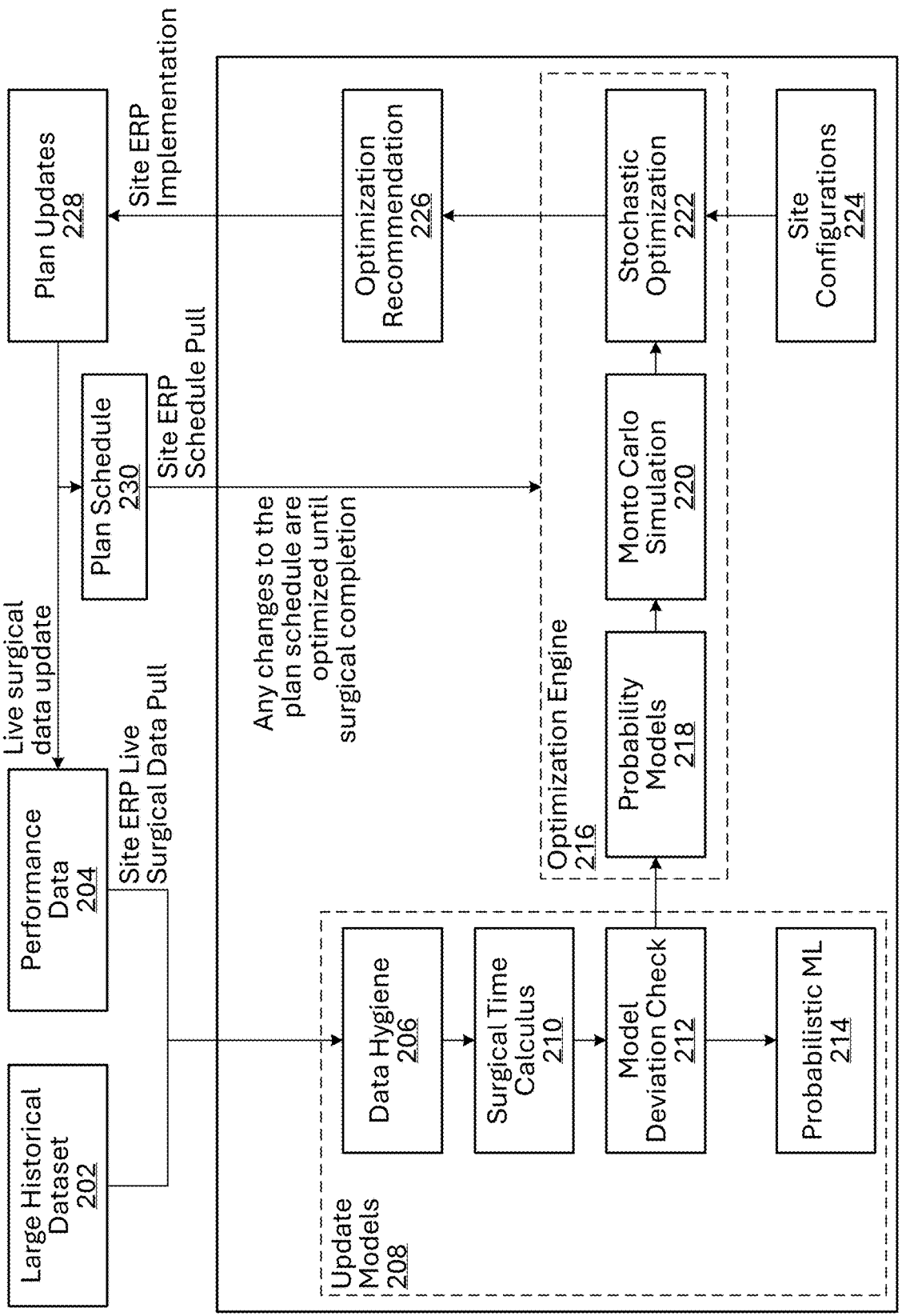
FIG. 2 illustrates a detailed schematic diagram of the exemplary patient service optimization procedure of FIG. 1.

Referring to FIGS. 1 and 2 simultaneously, FIG. 1 illustrates a flowchart for optimization of healthcare resource scheduling, and FIG. 2 illustrates a detailed patient service optimization system 200 which outlines the process at each step of FIG. 1. In an embodiment, the healthcare resource is a surgical operating room, which may be present in a hospital. In an embodiment, the healthcare resource includes a surgical operating room resource, such as the surgical operating room itself, medical equipment, and/or a healthcare practitioner. In an embodiment, the scheduled healthcare procedures are surgical procedures taking place in the surgical operating rooms of the hospital. In an embodiment, the surgical procedure includes the entire perioperative process of the surgical procedure. However, a person of skill in the art would recognize that this process could apply to other fields. For example, the healthcare resource could be a doctor, a surgeon, a procedure bed, an examination room, a dental chair, or any other resource which requires and makes use of a schedule and scheduling optimization using randomization methods. Similarly, the healthcare procedure does not need to be limited to surgical procedures, and could encompass procedures such as general health checkups, dental procedures, gynecology procedures, fluid tests, catheterization procedures, endoscopy procedures, interventional radiology procedures, or any other procedures which may require an appointment.

At step 102, data is received from the hospital systems. This includes a large historical dataset 202 that is collected from a secure client File Transfer Protocol (FTP) site. This historical dataset 202 can be collected directly from a hospital system database, or through a third-party monitoring system database. The historical dataset 202 contains variables and unique cases from a range of years, covering perioperative processes such as pre-anesthesia, patient positioning minutes (PPM) (also referred to as patient positioning duration), expected surgery duration, actual surgical duration, historical procedure volumes, post-anesthesia care, cancellation rates, and individual and combined surgical emergency rates. The historical dataset 202 may encompass many healthcare services such as general medicine, gynecology and obstetrics, orthopedic surgery, otolaryngology, and urology, among any other healthcare services that may require private rooms or appointment optimization.

Step 102 also includes collection of performance data 204, which includes Enterprise Resource Planning (ERP) data relating to live surgical data from the site database. This ERP data includes information such as daily operating room usage time, operating room Turn-Around-Time (TAT), operating room uptime, and surgeon uptime.

At step 104, the historical dataset 202 and the performance data 204 is fed into a machine learning model 206 to process and refine the data. A data hygiene step 208 may be performed to filter out data caused by noise such as patient cancellations or staffing issues, to determine whether data elements that deviate from an acceptable range are the result of noise. The surgical cases are categorized into different subcategories through the surgical time calculus 210. In an embodiment, the surgical time calculus involves a cluster analysis. In an embodiment, these subcategories may be low volume cases and high-volume cases. In a further embodiment, these subcategories may be determined using a Pareto analysis, in which the cases are divided into 80% and 20% variety. The Pareto analysis may take into account factors such as data volume by procedure, data volume by surgeon, and aggregated data volume for multiple procedures or surgeons.

Still in step 104, the model deviation check 212 may include multiple iterations to address different variables and factors, including but not limited to statistically significant differences between pre-Covid and post-Covid data, healthcare resource specialization, hospital site configuration, and various healthcare procedure specific differences and challenges. In an embodiment, the healthcare resource specialization may be a doctor or clinician specialization. The data may further surgical duration comparisons, procedure volume changes, and emergency cancellation rates. In an embodiment, model deviation check 212 may include Ad Hoc testing. The data following the model deviation check 212 may be fed into both a probabilistic machine learning model 214 as well as an optimization system 216.

The probabilistic machine learning model 214 may comprise a neural network. Neural networks will be briefly described in general terms. A neural network can include multiple layers of neurons, each neuron receiving inputs from a previous layer, applying a set of weights to the inputs, and combining these weighted inputs to generate an output, which can in turn be provided as input to one or more neurons of a subsequent layer.

A layer of neurons uses filters to define the relationship between the outputs of the neurons of the previous layer and the outputs of the neurons of the current layer. A layer of the neural network receives a data input, usually in the form of a data array of known dimensions. By applying the set of filters (layers) to the data input, each layer generates a data output, which is typically a data array having known dimensions. A filter comprises a set of weights (also called parameters).

Training a neural network involves learning or determining the appropriate weight values at different weight locations throughout the network. After being optimally trained to perform a given inference task, the weights of the neural network will not all contribute equally to the final inference outputs: some weights will have high value due to their high contribution, while other weights will have low value due to their low contribution. If the weights are not properly trained (e.g., high value weights are misplaced or miscalibrated by training), then the trained network will perform with less accuracy. The probabilistic machine learning model 214 can be trained by a suitable set of training data to determine appropriate weights. The training data may include the data as listed previously, and any other data that is necessary, including the historical dataset and performance data. The trained probabilistic machine learning model 214 can be used to create and apply models for performing inference tasks.

The probabilistic machine learning model 214 may include sub-models, which may be trained and used to predict sub-stages of the healthcare procedure. In an embodiment, the sub-models are trained and used to predict the duration of sequential perioperative sub-stages of a surgical procedure, including pre-anesthesia duration, patient positioning duration, surgery duration, and post-anesthesia duration. The predicted durations of each perioperative sub-stage may be aggregated into a combined expected completion time for a surgical procedure. The sub-models may also be trained and used to predict pre-anesthesia equipment usage, cancellation frequency for the surgical procedure, and/or surgical emergency frequency. Example of pre-anesthesia equipment include bed, chair, cart, intravenous bags, and medical instruments.

The probabilistic machine learning model and the sub-models may be further trained on a second set of training data, which may include a second processed historical dataset, the processed performance data, a second set of performance data, and the calculated duration of the sequential perioperative sub-stages of the procedures.

At step 106, optimization calculations are performed on the received data, beginning with the development of probability models 218. The probability models 218 may include models such as Poisson distributions for modeling large datasets, such as combined emergency surgical rates. Further distribution models may be created for variables such as surgical minutes (also known as surgical duration), PPM, general pre- and post-anesthesia care, and procedure specific pre- and post-anesthesia care.

Before performing Monte Carlo simulations 220, data is collected on elective surgery cancellations. In an embodiment, this data is categorized by surgical procedure, time before surgery, and frequency of cancellation. In an embodiment, this data may be further categorized by the day of the week during regular operation hours. In an embodiment, a binomial distribution may be used to determine the average weekly surgical cancellation frequency based on day of the week.

The Monte Carlo simulations 220 are used to calculate the collective time for surgeries. Using the data provided previously, a cancellation model is developed for integration into the Monte Carlo simulations 220. The cancellation model may include data relating to frequency, duration, and day of cancellation. In an embodiment, the Monte Carlo simulations 220 are applied over a number of iterations. In an embodiment, the Monte Carlo simulations 220 are applied over at least 10,000 iterations. The Monte Carlo simulations 220 are further used to predict the expected completion time for an operating room based on procedure duration, procedure cancellation expectancy, turn around time, and any other factors listed previously. In an embodiment, the Monte Carlo simulations 220 use and generate data that is specific to a surgeon, an activity, or a procedure. In an embodiment, the Monte Carlo simulations 220 further or alternatively use and generate data that is specific to an anesthetist. In an embodiment, the expected completion time is further calculated by aggregating the predicted duration of the sequential perioperative sub-stages of the surgical procedure that are calculated by the sub-models of the probabilistic machine learning model 214.

The data from the Monte Carlo simulations 220 is fed into a stochastic optimization process 222, designed to optimize the time and resources in a hospital within the end-to-end perioperative process. If not previously introduced, the stochastic optimization process 222 may use data relating to the site configuration of the hospital 224 to determine optimizations for room allocations. The stochastic optimization process 222 uses the results from the Monte Carlo simulations 220 to compute the aggregate of the entire day's estimated surgical procedure durations. In an embodiment, the calculation is processed and output as a cumulative distribution. In an embodiment, the 50th percentile of the cumulative distribution is used as the estimated surgery duration.

Using stochastic optimization 222 in conjunction with Monte Carlo simulations 220 increase the accuracy of the stochastic optimization process 222 by incorporating probabilistic and random elements.

At step 108, an optimization recommendation 226 is provided based on the computed data. This optimization recommendation may include scheduling a surgical procedure during an available time slot in an operating room, based on a schedule at least in part determined by the optimization calculations. For example, if a surgery is scheduled at 11 am in an operating room, and a second surgery is scheduled at 2 pm in the same operating room, and the first surgery is estimated to take 1.5 hours, the optimization recommendation may schedule a surgery that is estimated to take 1 hour in between the two surgeries that are already scheduled. Alternatively, if a first surgery is scheduled at 11 am in an operating room, and a second surgery is scheduled at 1 pm, but the first surgery is estimated to take 2.5 hours based on historical data, one of the two surgeries may be moved based on availability. The availability for procedures may be further dependent on the relative importance of a procedure, or availability of a specialized practitioner or surgeon to perform the procedure.

Finally, at step 110, the optimization recommendations 226 can be provided to the hospital through, for example, an enterprise resource planning (ERP) system. The live surgical data generated as a result of the optimizations can be used as input to run a new simulation.

Figure 3:
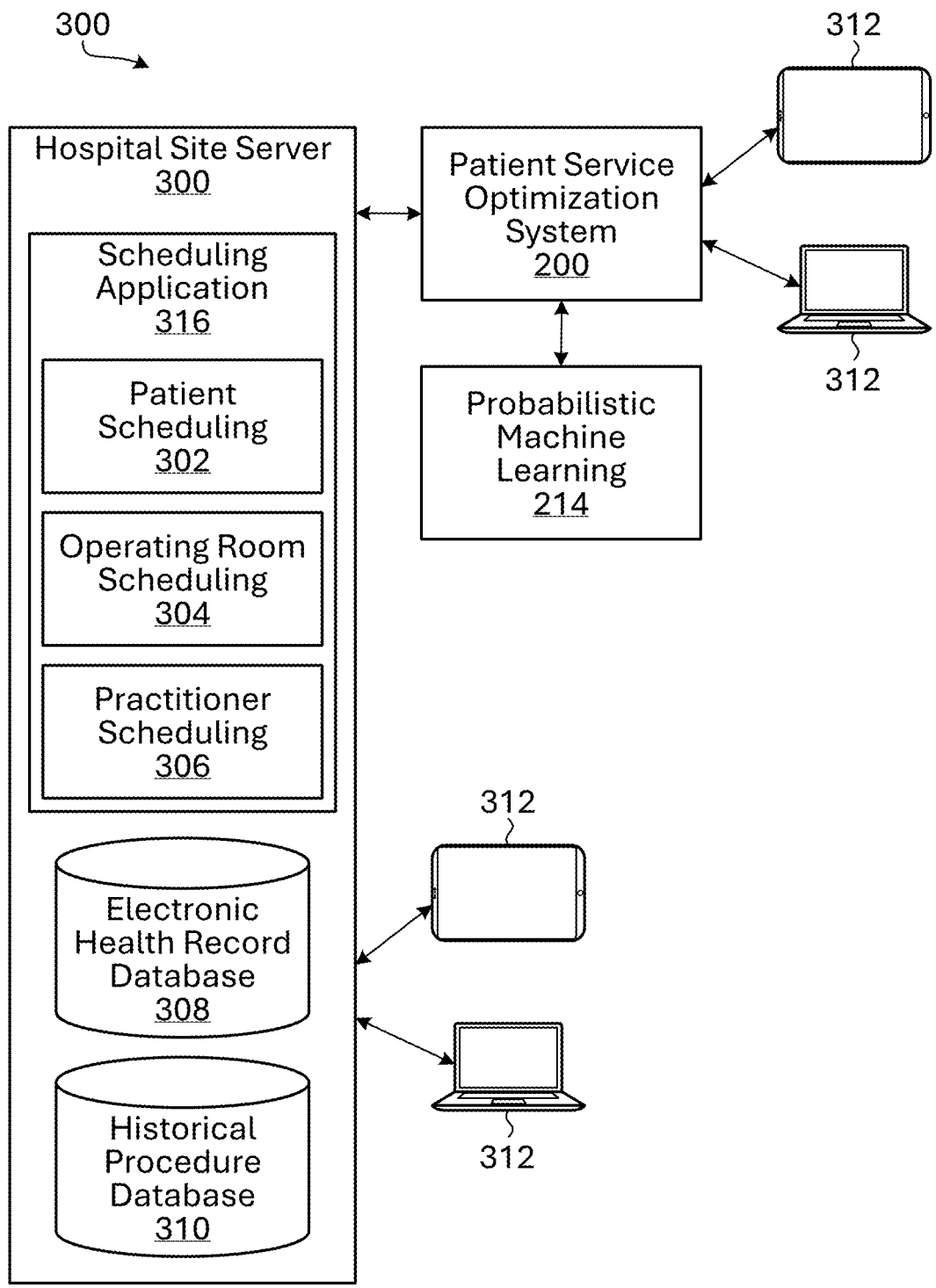
FIG. 3 illustrates an exemplary hospital site server, in which the patient service optimization system of FIG. 2 can be integrated.

FIG. 3 illustrates an example hospital server system 330, in accordance with an example embodiment. The hospital server system 330 may include the hospital site server 300, and one or more devices 312. In an embodiment, the hospital site server 300 includes an electronic health record database 308, a historical procedure database 310, and a scheduling application 316. The electronic health record database 308 may include data relating to patient information, status, previous care, medication, and any other information that is relevant to their care. The historical procedure database 310 may include data related to previously executed surgeries, including duration, cancellations, operating surgeon, and pre- and post-operation care. This information may be manually entered, or may be automatically updated after each surgery. The electronic health record database 308 and the historical procedure database 310 may be stored locally on hospital servers, or may be stored by a third party on, for example, a cloud server.

The scheduling application 316 may include a patient scheduling module 302, an operating room scheduling module 304, and a practitioner scheduling module 306. The patient scheduling module 302 may contain information relating to patient scheduling on a per patient basis, such as upcoming procedures, previous issues, time waiting for upcoming procedures, previous cancellations, and previous procedures. The patient scheduling module 302 may further contain general scheduling information, such as total number of upcoming procedures, total number of procedures categorized by procedure type, current wait times for procedures, recent cancellations, and emergency procedures. The operating room scheduling module 304 may contain information relating to each operating room, such as upcoming procedures, downtime between procedures, operating room issues, and upcoming availability. The operating room scheduling module 304 may also include information relating to operating rooms such as location within the hospital, size, procedure eligibility, and accessibility. The practitioner scheduling module 306 may include information relating to each healthcare practitioner, such as specialty, previous surgical history, upcoming procedures, downtime between procedures, and upcoming availability.

The device 312 may be an electronic device or user equipment for interacting with the user and for communicating with the hospital site server 300. In examples, the device 108 can be used by patients, hospital staff, or healthcare practitioners to access the hospital site server 300. The device 312 can be a desktop computer, a laptop, or a mobile communication device, such as a tablet. The device 312 may include an operating system (not shown), for example Android™, iOS™, Microsoft Windows™, or other appropriate operation systems. In some examples, the device 312 may include an input/output (IO) interface which is configured to interface with the user, for example via a touch screen, keyboard, buttons, microphone, speaker, etc.

The hospital site server 300 communicates with, provides data to, and receives data from the patient service optimization system 200. The hospital site server 300 may provide raw data to the patient service optimization system 200 in the form of information related to the historical procedure database 310, information related to the electronic health record database 308, and information from the scheduling application 316. The hospital site server 300 may receive data from the patient service optimization 200 in the form of optimization recommendations 226 related to scheduling application 316. the patient service optimization system 200 includes a probabilistic machine learning model 214 which is configured to automatically update and perform the optimization process outlined in FIG. 1 and FIG. 2.

In an embodiment, hospital staff or healthcare practitioners may be able to communicate with and view results from the patient service optimization system through a website, interactable web interface, or graphical user interface, accessible via device 312. This allows staff and practitioners to view appointment openings, new scheduled procedures, estimated duration, operating room efficiency, and practitioner uptime. In an embodiment, the patient service optimization system 200 may provide recommendations for increases in efficiency, such as procedures where the TAT can be optimized.

Figure 4A:
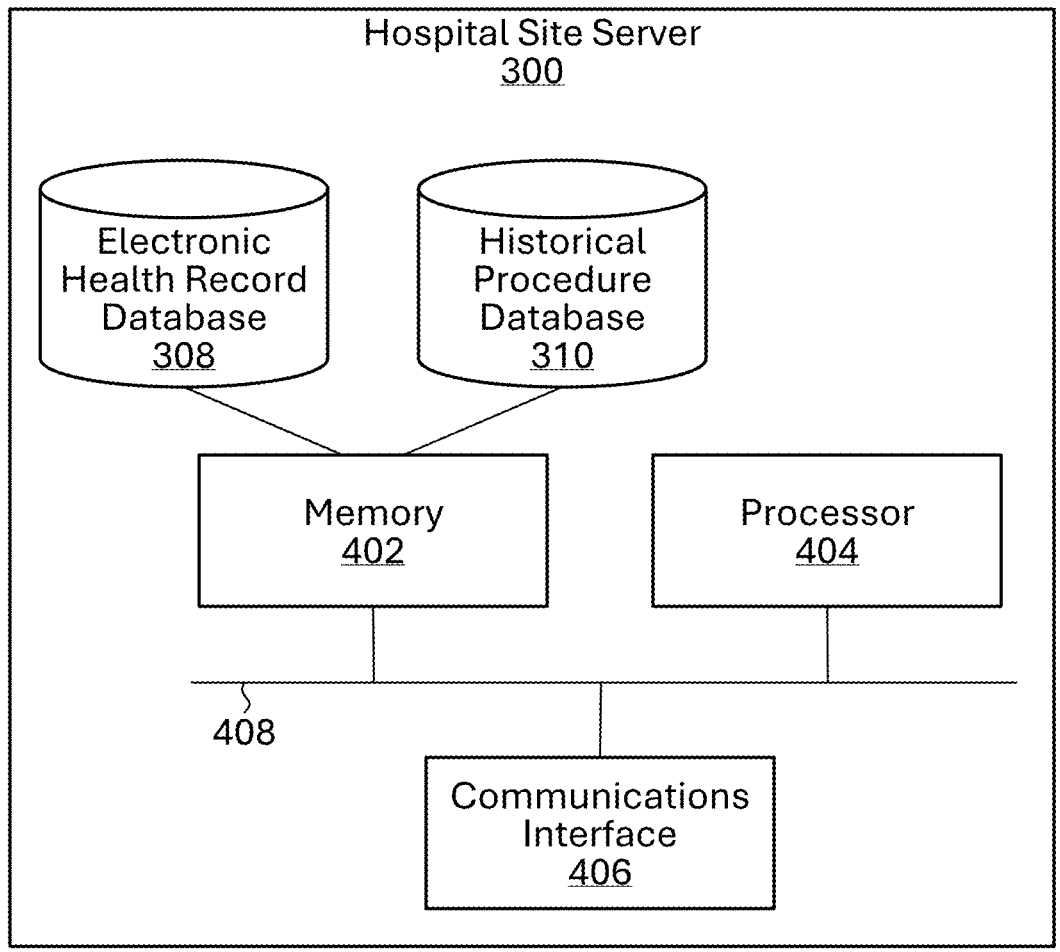
FIG. 4A illustrates a block diagram of the server in FIG. 3, according to an example embodiment.

FIG. 4A is a schematic diagram of a hardware structure of the hospital site server 300 according to an example embodiment. The hospital site server 300 shown in FIG. 4A includes a memory 402, a processor 404, a communications interface 406, and a bus 408. A communication connection is implemented between the memory 402, the processor 404, and the communications interface 406 by using the bus 404.

The processor 404 is configured to perform, when the program stored in the memory 402 is executed by the processor 404, steps of the method of site optimization as described herein.

The memory 402 can be a read-only memory (Read Only Memory, ROM), a static storage device, a dynamic storage device, or a random-access memory (Random Access Memory, RAM). The memory 402 may store a program. The memory 402 can be a non-transitory memory. The memory 402 can be external or removable in some examples. In an example, the memory 402 includes the electronic health record database 308 and the historical procedure database 310. In an example, the memory 402 includes the scheduling application 316.

The processor 404 can be a general central processing unit (Central Processing Unit, CPU), a microprocessor, an application-specific integrated circuit (Application Specific Integrated Circuit, ASIC), a graphics processing unit (graphics processing unit, GPU), or one or more integrated circuits.

In addition, the processor 404 may be an integrated circuit chip with a signal processing capability. In an implementation process, steps of the method of site optimization as described herein can be performed by an integrated logical circuit in a form of hardware or by an instruction in a form of software in the processor 404. In addition, the processor 404 can be a general purpose processor, a digital signal processor (Digital Signal Processor, DSP), an application-specific integrated circuit (ASIC), a field programmable gate array (Field Programmable Gate Array, FPGA) or another programmable logic device, a discrete gate or a transistor logic device, or a discrete hardware assembly. The processor 404 can implement or execute the methods, steps, and logical block diagrams that are described in example embodiments. The general purpose processor can be a microprocessor, or the processor may be any conventional processor or the like. The steps of the method disclosed with reference to the example embodiments may be directly performed by a hardware decoding processor, or may be performed by using a combination of hardware in the decoding processor and a software module. The software module may be located in a mature storage medium in the art, such as a random access memory, a flash memory, a read-only memory, a programmable read-only memory, an electrically erasable programmable memory, or a register. The storage medium is located in the memory 402. The processor 404 reads information from the memory 402, and completes, by using hardware in the processor 404, the steps of method 100 as detailed in FIGS. 1 and 2.

The communications interface 406 implements communication between hospital site server 300 and another device or communications network by using a transceiver apparatus, for example, including but not limited to a transceiver. For example, the training data may be obtained by using the communications interface 406.

The bus 408 may include a path that transfers information between all the components of the hospital site server 300.

It should be noted that, although only the memory 402, the processor 404, and the communications interface 406 are shown in the hospital site server 300 in FIG. 4A, in a specific implementation process, a person skilled in the art should understand that the hospital site server 300 may further include other components that are necessary for implementing normal execution. In addition, based on specific needs, a person skilled in the art should understand that the hospital site server 300 may further include hardware components that implement other additional functions. In addition, a person skilled in the art should understand that the hospital site server 300 may include only a component required for implementing the embodiments, without a need to include all the components shown in FIG. 4A.

Figure 4B:
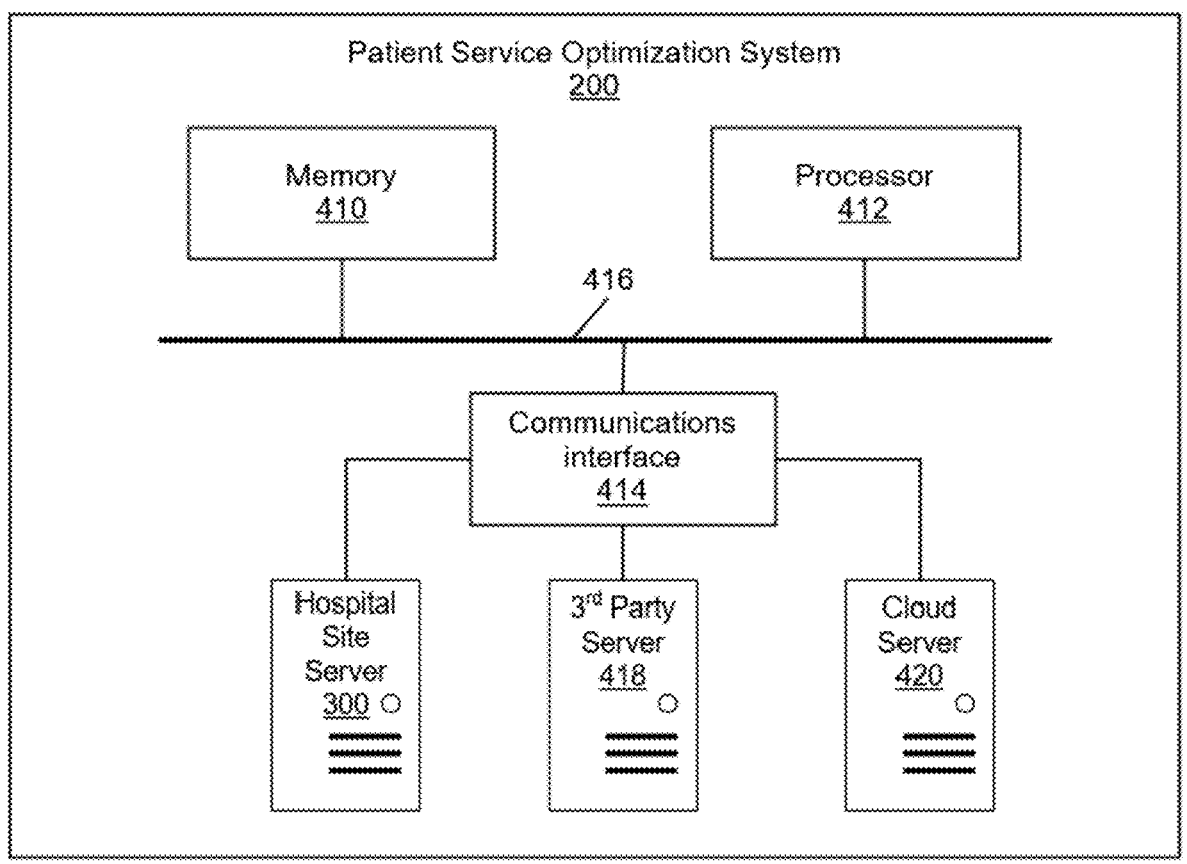
FIG. 4B illustrates a block diagram of the patient service optimization system of FIG. 2, according to an example embodiment.

Similar to the above, FIG. 4B provides an exemplary schematic diagram for the hardware structure of the patient service optimization system 200. The patient service optimization system 200 may include a memory 410, a processor 412, and a communications interface 414, connected by bus 416. A person of skill in the art should understand that patient service optimization system 200 may further include other components that are necessary for implementing normal execution. Notably, the patient service optimization system 200 can be implemented in different ways. In an embodiment, the patient service optimization system is on premises of the hospital, and cooperates with the hospital site server 300 to operate. In an embodiment, the patient service optimization system 200 cooperates with a $3^{rd}$ party server 418, for instance, a company server, to operate. In an embodiment, the patient service optimization system 200 cooperates with a cloud server 420 to operate.

Figure 5:
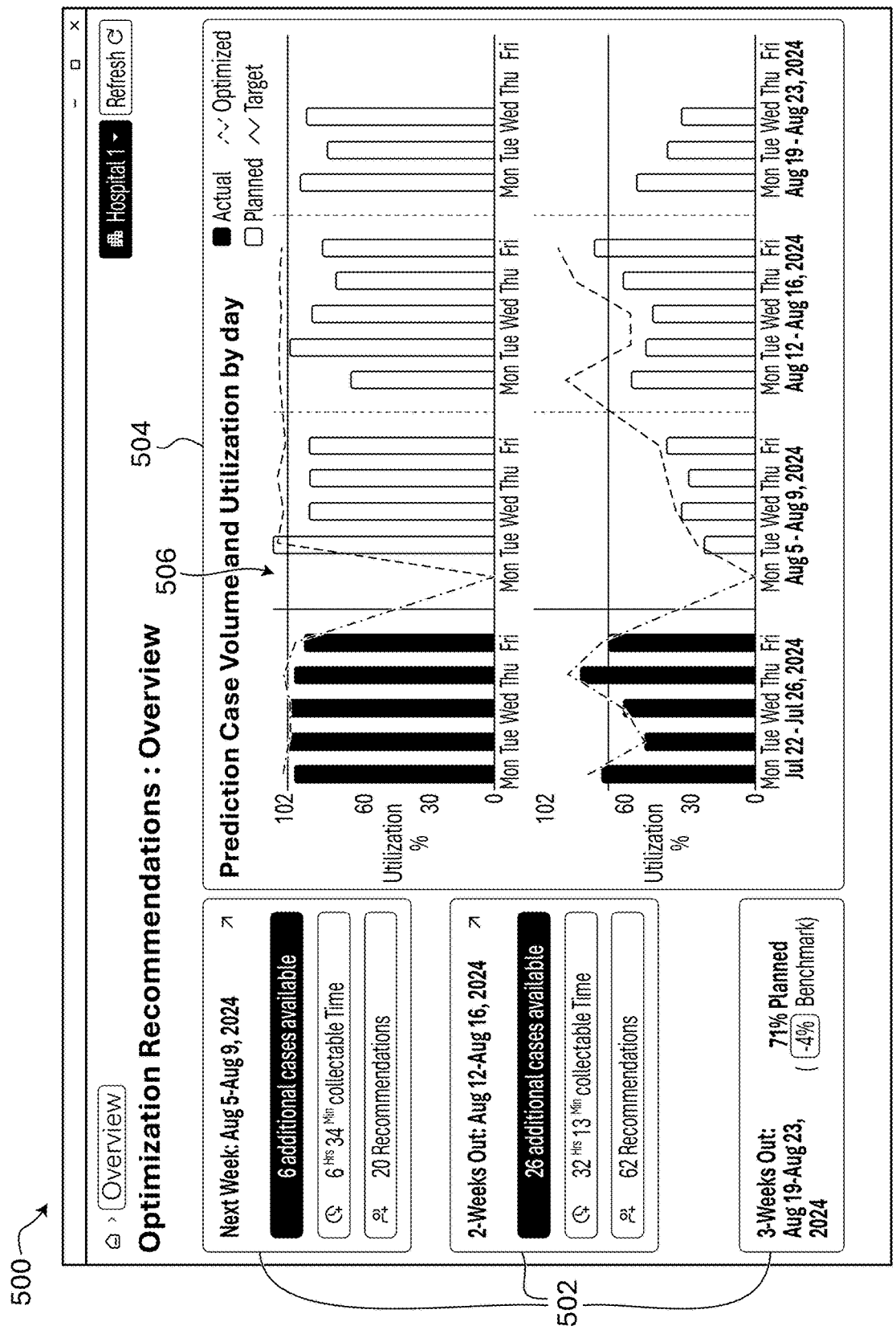
FIG. 5 illustrates an exemplary user interface for displaying optimization recommendations.

FIG. 5 illustrates an exemplary user interface 500 for displaying optimization recommendations 226 to a user. The exemplary user interface 500 may include weekly summaries 502, and a visualization of predicted case volume and utilization by day 504. The predicted case volume and utilization by day 504 may include utilization charts 506 which display the current and forecasted total utilization of the operating rooms.

The weekly summaries 502 may include information relating to additional procedures that can be scheduled, total collectable time (i.e., the amount of time that can be optimized), and optimization recommendations. The optimization recommendations may be in the form of recommending procedures during downtime to increase utilization. The predicted case volume and utilization by day 504 may display a visualization of utilization via utilization charts 506 for operating rooms in total. The utilization number may be expressed as a percentage, or may be expressed by any other metric or benchmark. A utilization number of below 100% may indicate that there is downtime in an operating room, and a utilization number above 100% may indicate that an operating room is overbooked, or will extend beyond typical working hours. The utilization charts 506 may further include a per day target utilization number. In an embodiment, the target utilization number is 100%. However, different target utilization numbers may be possible based on operating conditions such as staffing levels, holidays, emergencies, site renovations, operating room closures, and environmental factors. The utilization charts 506 may further include an optimized number, representing the utilization should the recommendations be implemented. The optimized number may be less than, equal to, or greater than the target utilization number. The actual utilization may be smaller than, equal to, or greater than the optimized number after implementing recommendations due to a variety of factors such as changes in TAT, unexpected roadblocks during surgical procedure, patient health concerns, operating room issues, or any other factors that may impact the total perioperative timeline.

Figure 6:
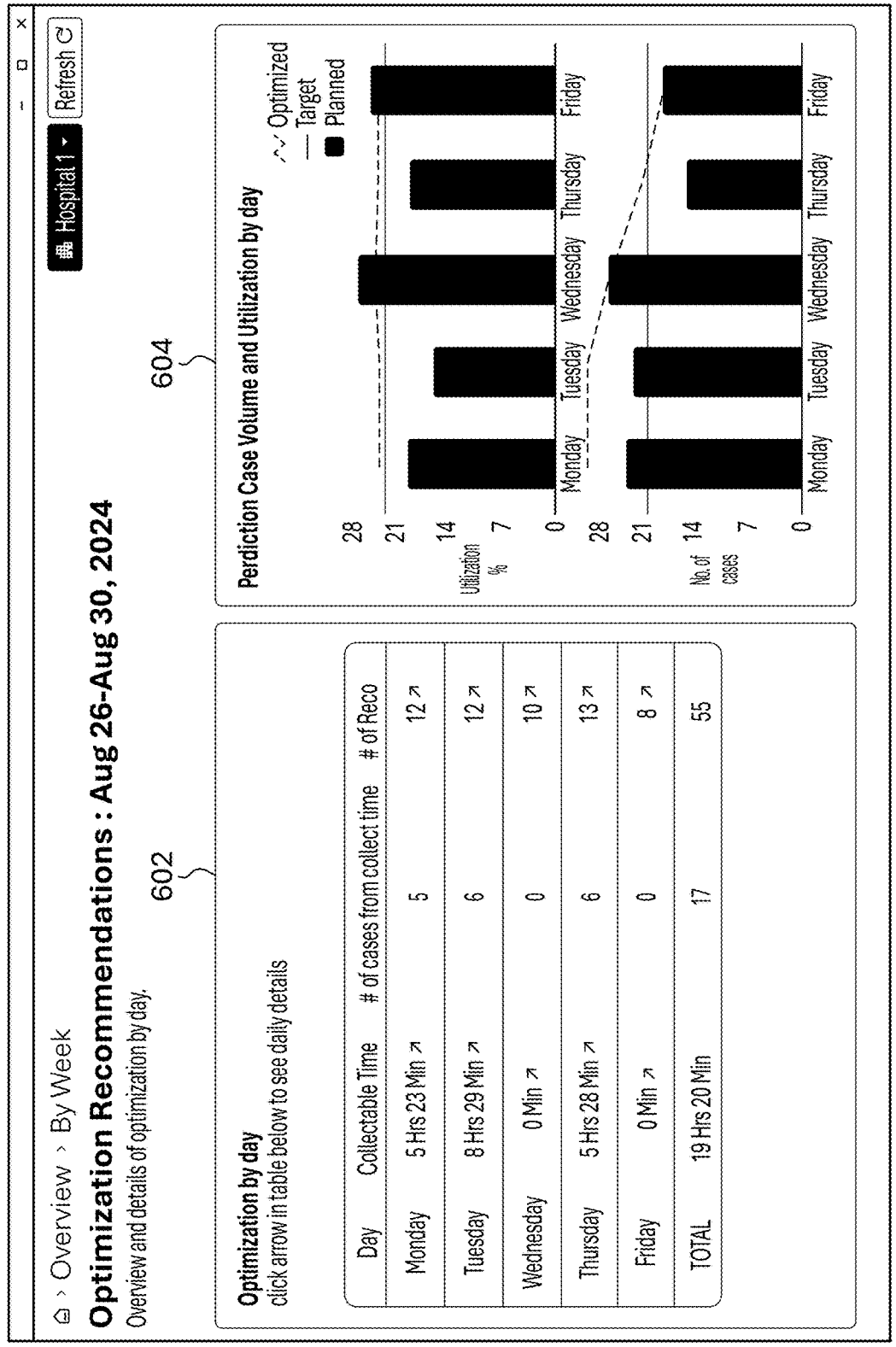
FIG. 6 illustrates an exemplary user interface for displaying detailed weekly optimization summaries.

FIG. 6 illustrates an exemplary user interface 600 in which the weekly summaries 502 are presented in more detail. User interface 600 may include more specific optimization results, such as daily statistics 602 and daily utilization and cases 604. Daily statistics may include total collectable time per day, total number of cases that can be implemented based on the collectable time per day, and total number of recommendations per day. These recommendations may be in the form of recommended surgical procedures in schedule to increase utilization of an operating room, or may be in the form of warnings relating to bed requirements, TAT, underutilization, overutilization, or any other warnings of events that may impede utilization of an operating room. The optimization dates may be limited to working days and typical working hours, or may include typical non-working days such as weekends and holidays. The daily utilization and cases 604 may include an illustration of total utilization by day as mentioned previously, alongside target utilization per day and an optimized number. The daily utilization and cases 604 may further include an illustration of total cases per day. This illustration may further include a target number of cases per day, which may change based on various factors as discussed previously. This illustration may further include an optimized number of cases per day, which may be above, equal to, or below the target number of cases per day.

Figure 7:
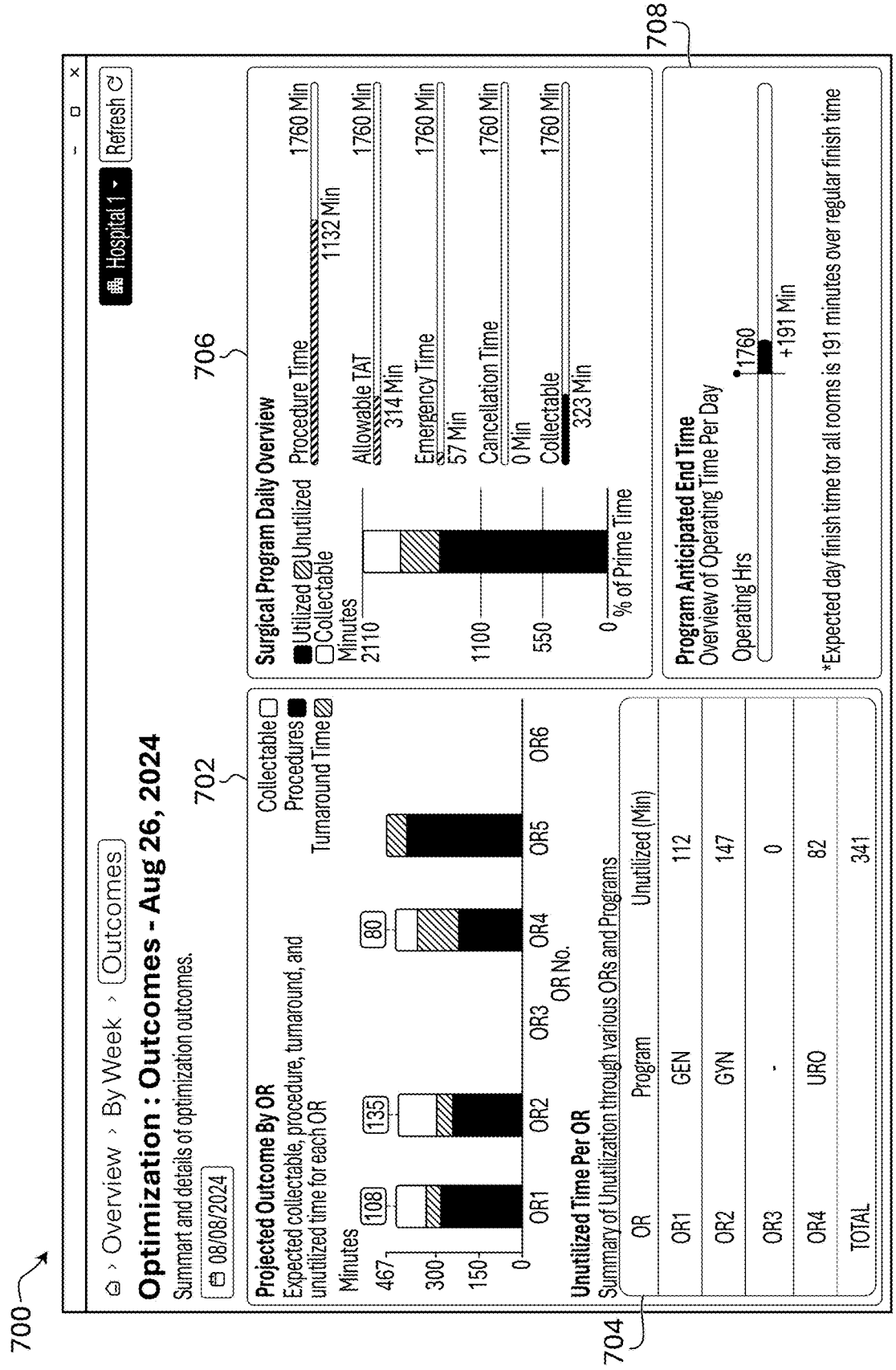
FIG. 7 illustrates an exemplary user interface for displaying daily optimization statistics.

FIG. 7 illustrates an exemplary user interface 700 in which the daily statistics 602 are presented in more detail. User interface 700 may include more specific optimization results, such as projected utilization by operating room 702, unutilized time by operating room 704, utilization overview 706, and anticipated end time 708. The projected utilization by operating room 702 may illustrate details related to projected outcomes on a per-operating room basis. The projected utilization by operating room 702 may further illustrate specifically how much time is devoted to procedures, TAT, and how much time is available as collectable time on a per-operating room basis. In an embodiment, the projected utilization by operating room 702 may display no collectable time if the total amount of collectable time is below a threshold, for example, an amount of time that is too small for any further surgical procedures to be scheduled. The unutilized time by operating room 704 displays the total unutilized time of an operating room, and may additionally include the program to which the operating room is assigned. As mentioned previously, the unutilized time by operating room 704 may display no unutilized time if the total amount of unutilized time falls below a certain threshold.

The utilization overview 706 may illustrate the total time utilization of the operating rooms. In an embodiment, the total time utilization may be divided unto utilized time, unutilized time, and collectable time. In an embodiment, the utilized time may be further divided into procedure time, allowable TAT, and emergency time. In an embodiment, the unutilized time may be further classified into cancellation time. In an embodiment, the collectable time represents the amount of unutilized time that can be utilized through optimization recommendations 226. As such, the collectable time may be equal to or less than the unutilized time. In an embodiment, the total time utilization may be expressed as a percentage of the total daily prime time (i.e., typical working hours). Anticipated end time 708 may display the anticipated end time of all procedures relative to the total amount of time for all operating rooms of typical working hours. The anticipated end time 708 may be less than, equal to, or greater than the number of typical working hours. The anticipated end time 708 may be represented as a number of minutes or hours, or may be represented as a percentage of typical working hours.

FIG. 8 illustrates an exemplary user interface 800 in which specific recommendations are made for each day. The user interface 800 may include recommendations 802 and warnings 804. The recommendations 802 may include details for candidate surgical procedures to be scheduled to increase utilization of operating rooms, such as operating room, program, surgeon, recommendation type, case type, utilization, and impact. The recommendation type may be to add a case, remove a case, move a case, or any other type of recommendation that would have a notable positive effect on utilization. The utilization may be displayed in the form of a percentage increase, or a time increase (e.g., hours, minutes, or both). Similarly, the impact may be displayed in the form of a time increase (e.g., hours, minutes, or both), or in the form of a percentage increase. In an embodiment, there may be space to implement all recommendations on a given day. In another embodiment, there may be multiple options for recommendations to increase utilization. In an embodiment, the recommendations which increase utilization the most are automatically selected.

The warnings 804 displayed in user interface 800 may be actionable warnings, or informative warnings. In an embodiment, an actionable warning may alert a user that there are opportunities for increases in utilization by employing one or more of the listed recommendations 802. In an embodiment, an informative warning may preemptively alert a user that certain adherence to certain guidelines or best practices is required to maximize utilization. These guidelines may be related to timing, cleanup procedures, anesthesia, or any other controllable variables related to the perioperative process.

Figure 9:
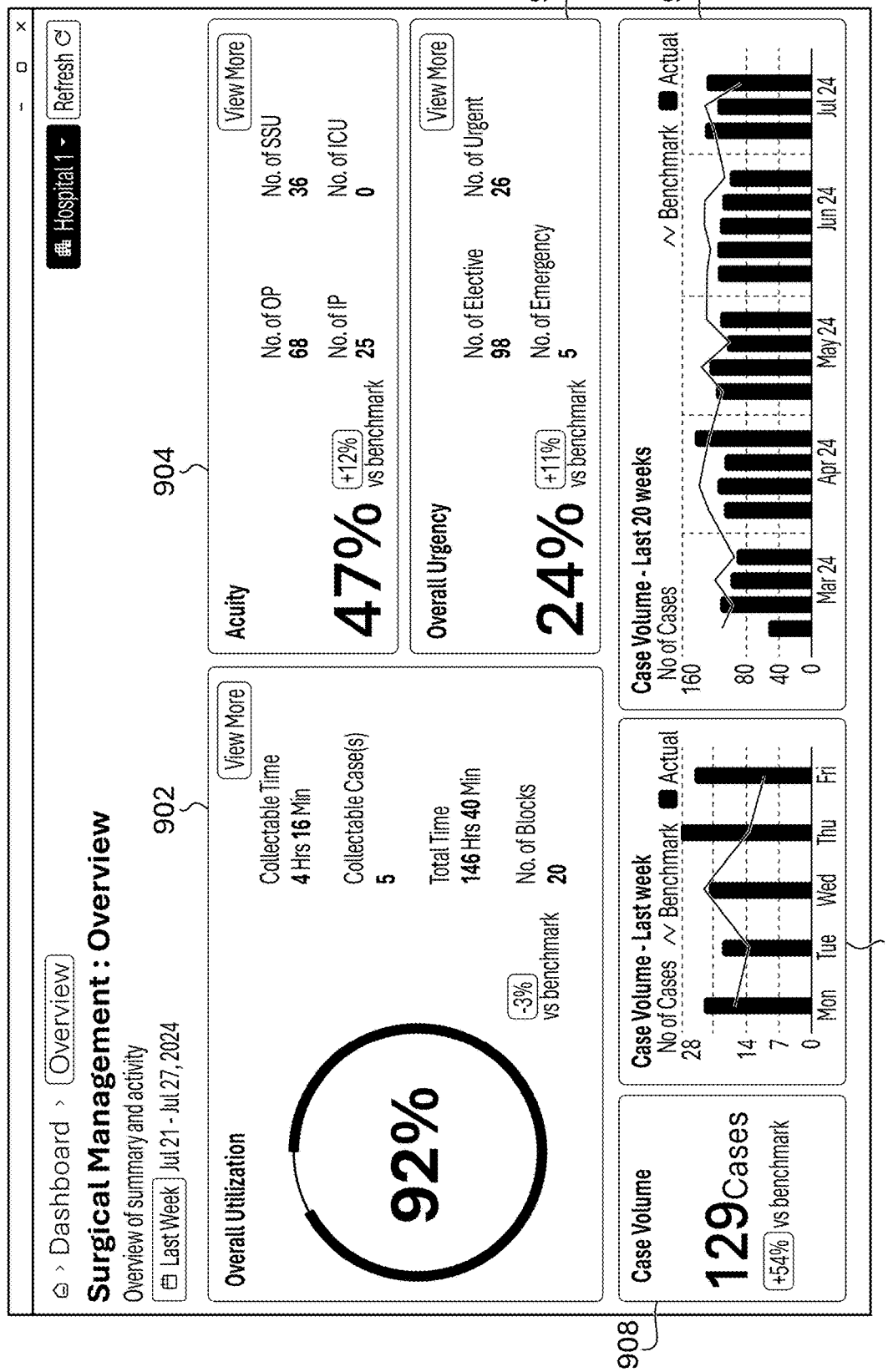
FIG. 9 illustrates an exemplary user interface for providing a healthcare management overview.

FIG. 9 illustrates an exemplary user interface 900 in which an overall management overview is provided to the user. In an embodiment, the user interface 900 includes an overall utilization 902, an overall acuity 904, an overall urgency 906, an overall case volume 908, a weekly case volume 910, and an extended case volume 912. The overall utilization 902 may provide a total utilization value for all operating rooms combined. In an embodiment, this number may be expressed in the form of a percentage. This number may be lower than, equal to, or higher than 100%. The overall utilization 902 may include a total collectable time for all operating rooms combined, as well as a total number of collectable cases, which can be scheduled into unutilized time blocks in an operating room during implementation of recommendations. The overall utilization 902 may further include information related to the total uptime of all operating rooms, as well as the number of surgical blocks of all operating rooms. In an embodiment, the overall utilization 902 may display a benchmark value for the total utilization value. This benchmark value may be fixed, or may fluctuate based on operating room availability, month, season, staffing, or any other variables that may affect total utilization. In an embodiment, the benchmark value is displayed as a percentage.

The overall acuity 904 may represent the total number of cases at a hospital. In an embodiment, the overall acuity 904 may categorize cases based on different classifiers. In an embodiment, the overall acuity 904 may categorize cases based on severity. For example, the overall acuity 904 may list the number of outpatients, the number of inpatients, the number of patients in a short stay unit, the number of patients in an intensive care unit, and/or any other relevant classification of patient types. The total acuity value may represent the ratio of surgical admission versus the total surgical case volume and may be represented by a percentage. In an embodiment, the overall acuity 904 may display a benchmark value for the total acuity value. This benchmark value may be fixed or may fluctuate based on variables as listed above.

The overall urgency 906 may display the ratio of surgical patients that require unplanned intervention, and further may display a total urgency value which may be represented as a percentage. The overall urgency 906 may also display the total number of surgeries, and may be categorized based on different classifiers, such as level of urgency. The overall urgency 906 may list the number of elective surgeries, the number of emergency surgeries, the number of urgent surgeries, and/or any other relevant classification of surgery types. In an embodiment, the overall urgency 906 may display a benchmark value for the total urgency value, which may be fixed or may fluctuate based on variables as described above.

The overall case volume 908 may display the total number of cases being handled by the hospital at the time. The total number of cases may be represented by a number, or may be represented as a percentage based on a threshold number. The overall case volume 908 may also include a benchmark value for the total number of cases. This benchmark value may be displayed as a number, or may be displayed as a percentage relative to the total case number. The benchmark value may be fixed or may fluctuate based on variables as described above. The weekly case volume 910 may display an average number of cases over a week in a similar manner as overall case volume 908, or may display individual data for each day of the week. In an embodiment, the individual daily data may be displayed in the form of a chart or graph. The weekly case volume 910 may include a benchmark value, which may be represented as a number, or may be illustrated on the chart or graph. Extended case volume 912 may similarly be represented as an average number of cases over a period of time, or may display individual data on a daily, weekly, or monthly basis. In an embodiment, the individual data may be displayed in the form of a chart or graph. The benchmark value may be represented as a number, or may be illustrated on the chart or graph.

Figure 10:
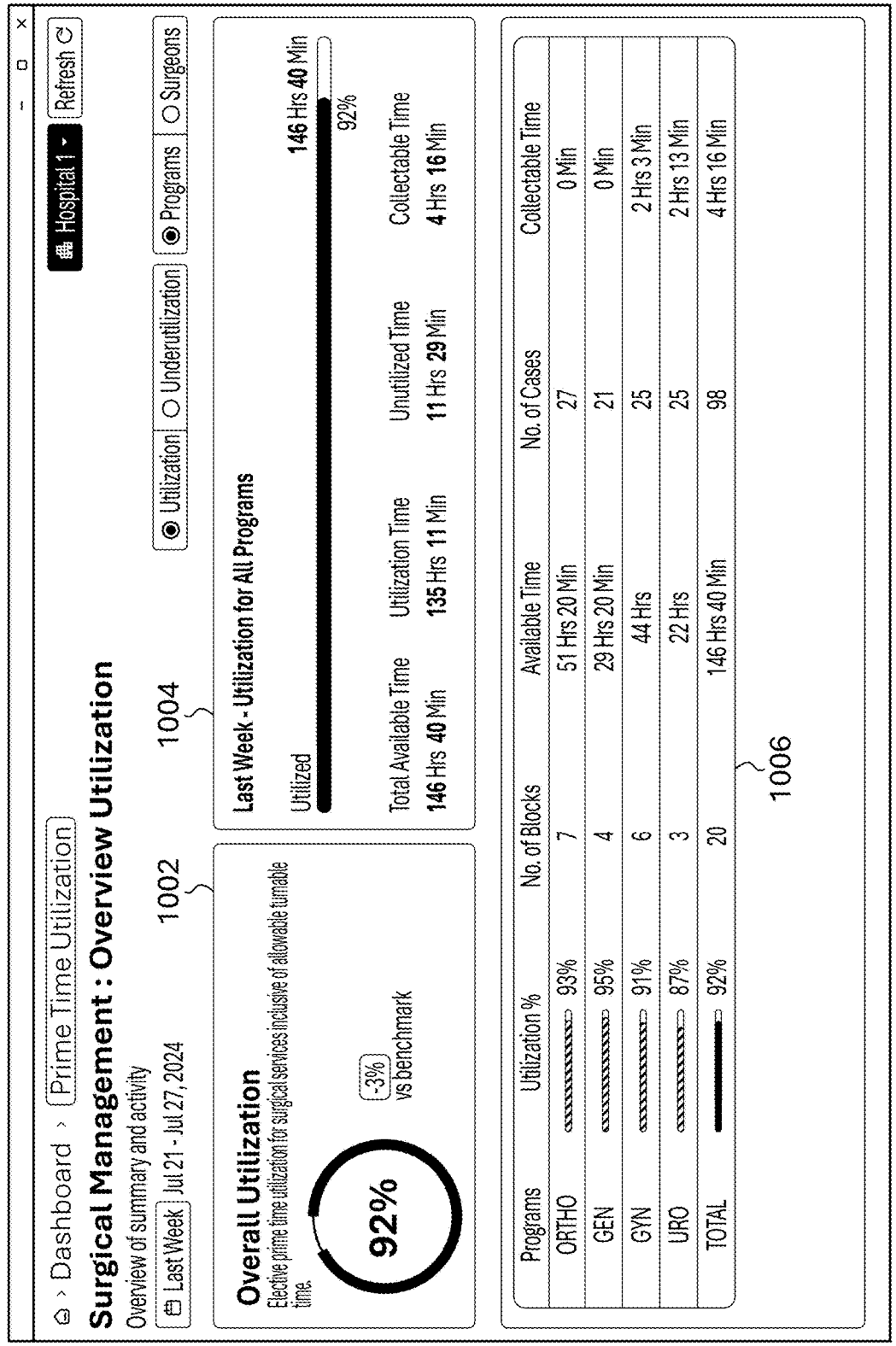
FIG. 10 illustrates an exemplary user interface for providing program utilization statistics.

FIG. 10 illustrates an exemplary user interface 1000 in which an overview of program utilization is presented to a user. The user interface 1000 may include a utilization summary 1002, a utilization time 1004, and a program utilization chart 1006. The utilization summary 1002 may provide similar information to overall utilization 902. Utilization time 1004 may display information such as the total available time for all operating rooms, the total utilized time for all operating rooms, the unutilized time for all operating rooms, the collectable time for all operating rooms, and/or any other utilization measurements that are relevant. In an embodiment, the percentage of utilized time may be visually represented. In an embodiment, the available time, utilized time, unutilized time, and collectable time is displayed for each individual operating room. Program utilization chart 1006 may display utilization information for each program, such as total utilization, number of appointment blocks, available time, number of cases, and collectable time. In an embodiment, the program utilization may include a total value for each of the above statistics. Where there is no unutilized time to fill, or no appointments to fill the unutilized time, the program utilization chart 1006 may display that there is no collectable time for a program.

FIG. 11 illustrates an exemplary user interface 1100 which presents an overview of surgeon utilization. In an embodiment, the surgeons are categorized by practice area. The overview of surgeon utilization may include information related to total utilization, number of appointment blocks, available time, number of cases, collectable time, and/or any other relevant utilization information. The utilization of each surgeon may be represented as a percentage relative to a threshold value, or may be represented as a number. Where there is no unutilized time to fill, or no appointments to fill the unutilized time, the overview of surgeon utilization may display no collectable time for a surgeon.

In the example embodiments, it should be understood that the system 200, hospital site server, and optimization methods may be implemented in other manners. For example, the described hospital site server is merely an example embodiment. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected according to actual requirements to achieve the objectives of the solutions of the embodiments.

In addition, functional units in the example embodiments may be integrated into one processing unit, or each of the units may exist alone physically, or two or more units are integrated into one unit.

When the functions are implemented in the form of a software functional unit and sold or used as an independent product, the functions may be stored in a computer-readable storage medium. Based on such an understanding, the technical solutions of example embodiments may be implemented in a form of a software product. The software product is stored in a storage medium, and includes several instructions for instructing a computer device (which may be a personal computer, a server, or a network device) to perform all or some of the steps of the methods described in the example embodiments. The foregoing storage medium includes any medium that can store program code, such as a Universal Serial Bus (USB) flash drive, a removable hard disk, a read-only memory (Read-Only Memory, ROM), a random access memory (Random Access Memory, RAM), a magnetic disk, or an optical disc.

In the described methods or block diagrams, the boxes may represent events, steps, functions, processes, modules, messages, and/or state-based operations, etc. While some of the above examples have been described as occurring in a particular order, it will be appreciated by persons skilled in the art that some of the steps or processes may be performed in a different order provided that the result of the changed order of any given step will not prevent or impair the occurrence of subsequent steps. Furthermore, some of the messages or steps described above may be removed or combined in other embodiments, and some of the messages or steps described above may be separated into a number of sub-messages or sub-steps in other embodiments. Even further, some or all of the steps may be repeated, as necessary. Elements described as methods or steps similarly apply to systems or subcomponents, and vice-versa. Reference to such words as "sending" or "receiving" could be interchanged depending on the perspective of the particular device.

The above discussed embodiments are considered to be illustrative and not restrictive. Example embodiments described as methods would similarly apply to systems, and vice-versa.

The various embodiments presented above are merely examples and are in no way meant to limit the scope of this disclosure. Variations of the innovations described herein will be apparent to persons of ordinary skill in the art, such variations being within the intended scope of the present disclosure. In particular, features from one or more of the above-described embodiments may be selected to create alternative embodiments comprises of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover all suitable changes in technology.

What is claimed is:

1. A method of scheduling, comprising:
receiving historical data and live operating data relating to at least one healthcare procedure, wherein the at least one healthcare procedure is at least one surgical procedure, the at least one surgical procedure corresponding to an entire perioperative process of the at least one surgical procedure, and wherein the live operating data includes live surgical data relating to a surgical procedure and a healthcare resource, including usage time of the healthcare resource, turn-around-time of the healthcare resource, and uptime of the healthcare resource;
processing the data using a machine learning model, wherein the processing comprises:
applying one or more probability models to the data, wherein the one or more probability models include actual surgical duration for each surgical procedure, procedure volume changes, cancellation rates for each surgical procedure, and combined emergency surgical rates,
performing one or more iterations of a Monte Carlo simulation on the data to calculate the collective time for provision of the at least one healthcare procedure,
applying a stochastic optimization to the one or more iterations of the Monte Carlo simulation, wherein the stochastic optimization process is based on a site configuration of a location containing the healthcare resource,
determining an expected completion time for each of the at least one healthcare procedure taking place with a healthcare resource, based on the results of the stochastic optimization, wherein the healthcare resource is an operating room, wherein the determining the expected completion time includes using sub-models of the machine learning model to predict duration of sequential perioperative sub-stages of each of the at least one surgical procedure, wherein the duration of the sequential perioperative sub-stages include, in sequence: pre-anesthesia duration, patient positioning duration, surgery duration, and post anesthesia duration, and wherein the determining the expected completion time includes aggregating the predicted duration of the sequential perioperative sub-stages for each of the at least one surgical procedure, and
determining, based on the expected completion time for each of the at least one healthcare procedure taking place with the healthcare resource, availability for one or more healthcare procedures with the healthcare resource, wherein determining the availability for one or more healthcare procedures is based on duration of the one or more healthcare procedures, importance of the one or more healthcare procedures, and availability of the one or more healthcare resources; and
generating a schedule of the one or more healthcare procedures to take place with the healthcare resource.

2. The method of claim 1, wherein the determining the expected completion time of each of the at least one surgical procedure includes using sub-models of the machine learning model to predict pre-anesthesia equipment usage, cancellation frequency, and/or surgical emergency frequency.

3. The method of claim 1, wherein the Monte Carlo simulations are applied over at least 10,000 iterations.

4. The method of claim 1, wherein the cancellation rates for each surgical procedure are categorized based on the day of the week.

5. The method of claim 2, wherein cancellation frequency is calculated based on a binomial distribution.

6. The method of claim 1, wherein the combined emergency surgical rates are modeled using a Poisson distribution.

7. The method of claim 1, wherein the stochastic optimization process accounts for uncertainty in variables related to pre-Covid and post-Covid differences, healthcare resource specialization, and/or healthcare procedure-specific differences.

8. The method of claim 1, further comprising generating for display the one or more healthcare procedures for at least one of a website, an interactable web page, or a graphical user interface.

9. A computer device, comprising:
a processor; and
memory containing instructions which, when executed by a processor, cause the processor to perform the method of claim 1.

10. A non-transitory memory containing instructions which, when executed by a processor, cause the processor to perform the method of claim 1.

* * * * *